US008559592B2

(12) United States Patent
Betcke et al.

(10) Patent No.: US 8,559,592 B2
(45) Date of Patent: Oct. 15, 2013

(54) SYSTEM AND METHOD FOR IMAGE RECONSTRUCTION BY USING MULTI-SHEET SURFACE REBINNING (75) Inventors: Marta Betcke, London (GB); William Robert Breckon Lionheart, Whaley Bridge (GB); Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 13/346,705

(22) Filed: Jan. 9, 2012

(65) Prior Publication Data

US 2012/0207374 A1    Aug. 16, 2012

Related U.S. Application Data (63) Continuation of application No. 12/835,682, filed on Jul. 13, 2010, now Pat. No. 8,204,173, which is a continuation-in-part of application No. 12/792,931, filed on Jun. 3, 2010, now Pat. No. 8,331,535, and a continuation-in-part of application No. 12/788,083, filed on May 26, 2010, now Pat. No. 8,451,974, and a continuation-in-part of application No. 12/787,878, filed on May 26, 2010, and a continuation-in-part of application No. 12/787,930, filed on May 26, 2010, now Pat. No. 8,223,919, and a continuation-in-part of application No. 12/758,764, filed on Apr. 12, 2010, (Continued)

(30) Foreign Application Priority Data

| Apr. 25, 2003 | (GB) | 0309371.3 |
|---|---|---|
| Apr. 25, 2003 | (GB) | 0309374.7 |
| Apr. 25, 2003 | (GB) | 0309379.6 |
| Apr. 25, 2003 | (GB) | 0309383.8 |
| Apr. 25, 2003 | (GB) | 0309385.3 |
| Apr. 25, 2003 | (GB) | 0309387.9 |
| Dec. 16, 2005 | (GB) | 0525593.0 |
| Jul. 15, 2008 | (GB) | 0812864.7 |
| Feb. 25, 2009 | (GB) | 0903198.0 |

(51) Int. Cl.
*A61B 6/00* (2006.01)

(52) U.S. Cl.
USPC .............................. 378/9; 378/4; 378/19

(58) Field of Classification Search
USPC ............................................. 378/4, 9, 10
See application file for complete search history.

(56) References Cited

U.S. PATENT DOCUMENTS 5,257,183 A   10/1993  Tam
6,240,157 B1   5/2001  Danielsson (Continued)

OTHER PUBLICATIONS

Rebinning-Based Algorithms for Helical Cone-Beam CT, Defrise et al., IOP Publishing, 2911-2937, 2001.

(Continued)

*Primary Examiner* — Alexander H Taningco
(74) *Attorney, Agent, or Firm* — Novel IP (57) ABSTRACT The present application is directed toward the generation of three dimensional images in a tomography system having X-ray sources offset from detectors, in particular in a system where the sources are located on a plane, while detectors are located on multiple parallel planes, parallel to the plane of sources and all the planes of detectors lie on one side of the plane of sources. A controller operates to rebin detected X-rays onto a non-flat surface, perform two dimensional reconstruction on the surface, and generate the three dimensional image from reconstructed images on the plurality of surfaces.

19 Claims, 4 Drawing Sheets

Related U.S. Application Data now Pat. No. 7,929,663, which is a continuation of application No. 12/211,219, filed on Sep. 16, 2008, now Pat. No. 7,724,868, which is a continuation of application No. 10/554,655, filed as application No. PCT/GB2004/001751 on Apr. 23, 2004, now Pat. No. 7,440,543, said application No. 12/835,682 is a continuation-in-part of application No. 12/712,476, filed on Feb. 25, 2010, now Pat. No. 8,243,876, and a continuation-in-part of application No. 12/697,073, filed on Jan. 29, 2010, now Pat. No. 8,085,897, which is a continuation of application No. 10/554,570, filed as application No. PCT/GB2004/001747 on Apr. 23, 2004, now Pat. No. 7,684,538, said application No. 12/835,682 is a continuation-in-part of application No. 12/651,479, filed on Jan. 3, 2010, now abandoned, which is a continuation of application No. 10/554,654, filed as application No. PCT/GB2004/001731 on Apr. 23, 2004, now Pat. No. 7,664,230, said application No. 12/835,682 is a continuation-in-part of application No. 12/485,897, filed on Jun. 16, 2009, now abandoned, which is a continuation of application No. 10/554,656, filed as application No. PCT/GB2004/001729 on Apr. 23, 2004, now Pat. No. 7,564,939, said application No. 12/835,682 is a continuation-in-part of application No. 12/478,757, filed on Jun. 4, 2009, now Pat. No. 8,094,874, which is a continuation of application No. 12/364,067, filed on Feb. 2, 2009, now abandoned, which is a continuation of application No. 12/033,035, filed on Feb. 19, 2008, now Pat. No. 7,505,563, which is a continuation of application No. 10/554,569, filed as application No. PCT/GB2004/001732 on Apr. 23, 2004, now Pat. No. 7,349,525, said application No. 12/835,682 is a continuation-in-part of application No. 12/371,853, filed on Feb. 16, 2009, now Pat. No. 7,903,789, which is a continuation of application No. 10/554,975, filed as application No. PCT/GB2004/001741 on Apr. 23, 2004, now Pat. No. 7,512,215, said application No. 12/835,682 is a continuation-in-part of application No. 12/364,067, filed on Feb. 2, 2009, now abandoned, which is a continuation of application No. 12/033,035, filed on Feb. 19, 2008, now Pat. No. 7,505,563, said application No. 12/835,682 is a continuation-in-part of application No. 12/097,422, filed as application No. PCT/GB2006/004684 on Dec. 15, 2006, now Pat. No. 7,876,879, said application No. 12/835,682 is a continuation-in-part of application No. 12/142,005, filed on Jun. 19, 2008, now Pat. No. 8,135,110.

(60) Provisional application No. 61/155,572, filed on Feb. 26, 2009, provisional application No. 61/181,068, filed on May 26, 2009, provisional application No. 61/181,077, filed on May 26, 2009, provisional application No. 61/181,070, filed on May 26, 2009, provisional application No. 61/183,591, filed on Jun. 3, 2009, provisional application No. 61/225,257, filed on Jul. 14, 2009.

(56) References Cited

U.S. PATENT DOCUMENTS

| | | | |
|---|---|---|---|
| 6,324,243 B1 | 11/2001 | Edic et al. | |
| 6,411,670 B1* | 6/2002 | Besson | 378/4 |
| 6,778,629 B1* | 8/2004 | Danielsson et al. | 378/15 |
| 7,142,628 B2* | 11/2006 | Grass et al. | 378/4 |
| 7,430,270 B2* | 9/2008 | Bontus et al. | 378/17 |
| 7,778,387 B2* | 8/2010 | Koehler et al. | 378/19 |
| 7,933,375 B2* | 4/2011 | Pack | 378/4 |
| 8,050,480 B2* | 11/2011 | Noo et al. | 382/131 |
| 2004/0066879 A1 | 4/2004 | Machida | |
| 2004/0179643 A1* | 9/2004 | Gregerson et al. | 378/4 |
| 2005/0123092 A1 | 6/2005 | Mistretta et al. | |
| 2005/0249432 A1 | 11/2005 | Zou et al. | |
| 2006/0050642 A1 | 3/2006 | Chini et al. | |
| 2006/0050842 A1* | 3/2006 | Wang et al. | 378/16 |
| 2008/0056435 A1* | 3/2008 | Basu et al. | 378/9 |
| 2011/0091007 A1* | 4/2011 | Betcke et al. | 378/4 |

OTHER PUBLICATIONS

Search Report for PCT/US10/41871, Jan. 20, 2011, Rapiscan Systems, Inc.

* cited by examiner

SYSTEM AND METHOD FOR IMAGE RECONSTRUCTION BY USING MULTI-SHEET SURFACE REBINNING

CROSS REFERENCE

The present invention relies on U.S. Provisional Patent Application No. 61/225,257, of the same title, and filed on Jul. 14, 2009, for priority.

The present application is also a continuation-in-part of U.S. patent application Ser. No. 12/485,897, filed on Jun. 16, 2009, which is a continuation of U.S. patent application Ser. No. 10/554,656, filed on Oct. 25, 2005, and now issued U.S. Pat. No. 7,564,939, which is a 371 national stage application of PCT/GB04/01729, filed on Apr. 23, 2004 and which, in turn, relies on Great Britain Application No. 0309387.9, filed on Apr. 25, 2003, for priority.

The present application is also a continuation-in-part of U.S. patent application Ser. No. 12/371,853, filed on Feb. 16, 2009, which is a continuation of U.S. patent application Ser. No. 10/554,975, filed on Oct. 25, 2005, and now issued U.S. Pat. No. 7,512,215, which is a 371 national stage application of PCT/GB2004/01741, filed on Apr. 23, 2004 and which, in turn, relies on Great Britain Application Number 0309383.8, filed on Apr. 25, 2003, for priority.

The present application is also a continuation-in-part of U.S. patent application Ser. No. 12/651,479, filed on Jan. 3, 2010, which is a continuation of U.S. patent application Ser. No. 10/554,654, filed on Oct. 25, 2005, and now issued U.S. Pat. No. 7,664,230, which is a 371 national stage application of PCT/GB2004/001731, filed on Apr. 23, 2004 and which, in turn, relies on Great Britain Patent Application Number 0309371.3, filed on Apr. 25, 2003, for priority.

The present application is also a continuation-in-part of U.S. patent application Ser. No. 12/364,067, filed on Feb. 2, 2009, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority.

The present invention is also a continuation-in-part of U.S. patent application Ser. No. 12/758,764, filed on Apr. 12, 2010, which is a continuation of U.S. patent application Ser. No. 12/211,219, filed on Sep. 16, 2008, and now issued U.S. Pat. No. 7,724,868, which is a continuation of U.S. patent Ser. No. 10/554,655, filed on Oct. 25, 2005, and now issued U.S. Pat. No. 7,440,543, which is a 371 national stage application of PCT/GB2004/001751, filed on Apr. 23, 2004, and which, in turn, relies on Great Britain Patent Application Number 0309385.3, filed on Apr. 25, 2003, for priority.

The present application is also a continuation-in-part of U.S. patent application Ser. No. 12/697,073, filed on Jan. 29, 2010, which is a continuation of U.S. patent application Ser. No. 10/554,570, filed on Oct. 25, 2005, and now issued U.S. Pat. No. 7,684,538, which is a 371 national stage application of PCT/GB2004/001747, filed on Apr. 23, 2004, and which, in turn, relies on Great Britain Patent Application Number 0309379.6, filed on Apr. 25, 2003, for priority.

The present application is also a continuation-in-part of U.S. patent application Ser. No. 12/097,422, filed on Jun. 13, 2008, and U.S. patent application Ser. No. 12/142,005, filed on Jun. 19, 2008, both of which are 371 national stage applications of PCT/GB2006/004684, filed on Dec. 15, 2006, which, in turn, relies on Great Britain Patent Application Number 0525593.0, filed on Dec. 16, 2005, for priority.

The present application is also a continuation-in-part of U.S. patent application Ser. No. 12/478,757, filed on Jun. 4, 2009, which is a continuation of U.S. patent application Ser. No. 12/364,067, filed on Feb. 2, 2009, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority. In addition, U.S. patent application number relies on Great Britain Patent Application Number 0812864.7, filed on Jul. 15, 2008, for priority.

The present application is also a continuation-in part of U.S. patent application Ser. No. 12/712,476, filed on Feb. 25, 2010, which relies on U.S. Provisional Patent Application No. 61/155,572 filed on Feb. 26, 2009 and Great Britain Patent Application No. 0903198.0 filed on Feb. 25, 2009, for priority.

The present application is also a continuation-in-part of U.S. patent application Ser. No. 12/787,930, filed on May 26, 2010, and which relies on U.S. Patent Provisional Application No. 61/181,068 filed on May 26, 2009, for priority.

The present application is also a continuation-in-part of U.S. patent application Ser. No. 12/788,083, filed on May 26, 2010, and which relies on U.S. Patent Provisional Application No. 61/181,070 filed on May 26, 2009, for priority.

The present application is also a continuation-in-part of U.S. patent application Ser. No. 12/787,878, filed on May 26, 2010, and which relies on U.S. Patent Provisional Application No. 61/181,077 filed on May 26, 2009, for priority.

The present application is also a continuation-in-part of U.S. patent application Ser. No. 12/792,931, filed on Jun. 3, 2010, and which relies on U.S. Patent Provisional Application No. 61/183,591 filed on Jun. 3, 2009, for priority.

Each of the aforementioned PCT, foreign, and U.S. applications, and any applications related thereto, is herein incorporated by reference in their entirety.

FIELD OF THE INVENTION

The present invention relates to methods for image reconstruction in which radiation is assumed to propagate along straight lines through an attenuating medium. More particularly, the present invention relates to a method of reconstructing images obtained from a cone beam tomography sensor in which detector positioning is restricted, and thus, offset through the presence of the multiple sources.

BACKGROUND

In a conventional cone beam X-ray computerized tomography (CB CT) system a source of radiation is placed opposite an array of detectors which are arranged in a manner such that the position of the detector array is fixed relative to the source. The source and detectors are then moved mechanically relative to an object being imaged. In some systems, the object is kept stationary and the source-detector assembly is moved, whereas in others the source and detectors are rotated around the object while the object is translated. Some systems are configured such that the source describes a helical trajectory relative to the object. The rate at which tomographic images can be acquired by such systems is limited by the rate of rotation of the assembly supporting the source and detector array.

In X-ray tomography systems such as in a Real Time Tomography (RTT) system for example, a plurality of X-ray sources are arranged around a circle, however more general arrangements of sources along curves encircling the region of interest are possible. These sources are switched on and off in a sequence in order to obtain the same effect as obtained from a single rotating radiation source. In such systems, a detector cannot be placed opposite a given source as that position is occupied by another source. This renders attenuation along rays that make less than a particular limiting angle to the plane of the sources immeasurable. Such systems maybe termed as "offset detector" systems.

In contrast to the conventional and standard helical cone beam tomography system, for such an "offset detector" system no plane exists in which attenuation along all rays are measured. Hence, a simple two dimensional inverse Radon transform cannot be used to reconstruct an image on that plane. One known method for regaining efficiency of two dimensional reconstructions for such a system is to approximate the line integrals along rays in a plane using integrals along rays that lie close to that plane. A more general method called surface rebinning is to approximate using lines close to a surface.

For a given detector array shape and size and source trajectory, it is possible to calculate an optimal rebinning surface using the fixed point algorithm known in the art. This method can also be used, with some modification, when the extent of the detector is limited, as is in offset systems, or more generally, systems where the detector is not symmetrical in an axial direction with respect to the active source. However in the case of an offset detector approximation with rays close to one surface can result in poor image reconstruction due to absence of rays making an acute angle to the source plane.

Hence, there is need for a method of reconstructing images from a tomographic system in which detectors are not located directly opposite radiation sources.

SUMMARY OF THE INVENTION

In one embodiment, the present invention is directed toward a tomography system comprising a plurality of X-ray sources and a plurality of detectors, which are offset from one other, wherein the plurality of sources lie in a first plane and the plurality of detectors lie in a plurality of planes parallel to the first plane of sources. The tomography system further comprises a controller adapted to process X-rays detected by said plurality of detectors and generate a three dimensional image wherein said controller comprises a plurality of programmatic instructions that, when executed, a) rebin each of said detected X-rays onto a non-flat surface, b) perform a two dimensional reconstruction of said rebinned data on a non-flat surface, and c) generate said three dimensional image from the said reconstructed images on the plurality of said surfaces.

Optionally, the controller filters said rebinned data to maximize resolution of said three dimensional image. The rebinning of each of said detected X-ray onto a non-flat surface is achieved by collecting data from X-rays close to a surface with more than one sheet and wherein reconstruction on each surface is subsequently achieved by applying at least one of a two-dimensional weighted inverse Radon transform or an adapted two-dimensional reconstruction, to combined data from all sheets.

The three dimensional image is derived from a set of simultaneously solvable equations relating a plurality of reconstructed superimposed images, one on each of a plurality of multi-sheet surfaces, and a plurality of z-positions of sheets of each multi-sheet surface intersecting each point in a region being imaged. The set of simultaneously solvable equations is solved using at least one of a least squares sense, a minimization of a sum of absolute values of residuals, a minimization of any weighted norm of residuals, a minimization of any weighted norm of residuals wherein said weights are derived from a model of data errors, structured Total Least Norms, Iteratively Reweighted Least Squares and Iteratively Reweighted Norm approaches, or optimization methods including primal-dual methods, gradient methods, gradient projection methods, nonlinear reconstruction methods, with any type of regularization, penalty or constraints.

The controller initiates the generation of said three dimensional image after a threshold amount of detected X-ray data are obtained prior to obtaining data for the entire object. The plurality of X-ray sources are stationary. The controller uses said set of simultaneous equations incorporating the direction point spread functions in an axial direction to improve approximation with detected X-rays which were at least partially not on a rebinning surface. The controller is adapted to perform backprojection without filtering on multi-sheet surfaces; axial deconvolution; and subsequently filtering on each transaxial slice of a volume being imaged. The controller is adapted to correct sinogram data on a rebinning surface using at least one of an optical flow technique or any Partial Differential Equation technique.

In another embodiment, the present invention is directed toward a method of generating a three dimensional image in a tomography system comprising a plurality of X-ray sources and a plurality of detectors, which are offset from one other, wherein the plurality of sources lie in a first plane and the plurality of detectors lie in a plurality of planes parallel to the first plane of sources, further comprising the steps of: a) rebinning each of said detected X-rays onto a non-flat surface, b) performing a two dimensional reconstruction of the said rebinned data on a non-flat surface, and c) generating said three dimensional image from the said reconstructed images on the plurality of said surfaces.

Optionally, the method further comprises the step of filtering said rebinned data to maximize resolution of said three dimensional image. The step of rebinning of each of said detected X-ray onto a non-flat surface is achieved by collecting data from X-rays close to a surface with more than one sheet and wherein the reconstruction on each surface is subsequently achieved by applying at least one of a two-dimensional weighted inverse Radon transform or any adapted two-dimensional reconstruction, to combined data from all sheets.

The step of generating the three dimensional image is performed by solving a set of simultaneously solvable equations relating a plurality of reconstructed superimposed images, one on each of a plurality of multi-sheet surfaces, and a plurality of z-positions of sheets of each multi-sheet surface intersecting each point in a region being imaged. The set of simultaneously solvable equations is solved using at least one of a least squares, a minimization of a sum of absolute values of residuals, a minimization of any weighted norm of residuals, a minimization of any weighted norm of residuals where said weights are derived from a model of data errors, structured Total Least Norms, Iteratively Reweighted Least Squares and Iteratively Reweighted Norm approaches, optimization methods including primal-dual methods, gradient methods, gradient projection methods, nonlinear reconstruction methods, with any type of regularization, penalty or constraints.

The method uses said set of simultaneous equations incorporating the direction point spread functions in an axial direction to improve approximation with detected X-rays which were at least partially not on a rebinning surface. The method includes the steps of performing backprojection without filtering on multi-sheet surfaces; axial deconvolution; and subsequently filtering on each transaxial slice of a volume being imaged. The method of generating said three dimensional image is initiated after a threshold amount of detected X-ray data are obtained well before the data for the entire object has been acquired. The method further comprises the step of correcting sinogram data on a rebinning surface using at least one of an optical flow technique or any Partial Differential Equation technique.

These and other embodiments and aspects of the disclosed inventions will be further detailed in the Detailed Description read in light of the drawings.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

The present invention provides a method of reconstructing images from a cone beam tomographic sensor in which detectors are not located directly opposite radiation sources. In one embodiment, the present invention applies to X-ray computerized tomography. More generally, the present invention applies to methods of image reconstruction, wherein, radiation is assumed to propagate along straight lines through an attenuating medium. In an embodiment, the method of the present invention may be applied to image reconstruction in systems using gamma rays. The method of reconstructing images uses data from rays close to a multi-sheet surface which may have a conical singularity where the sheets of the surface meet or the sheets may cross along contours. This data is reconstructed in a manner similar to reconstruction of data from rays in a plane, by using a two dimensional reconstruction algorithm on a plurality of sheets. The volumetric image is recovered by solving a system of simultaneous equations, each of which expresses the superposition condition for all sheets of a multi-sheet surface. Such a system is solvable due to a plurality of sheets intersecting each voxel.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention employs a surface with a plurality of sheets, which in one embodiment intersect each other. Further, line data is approximated on the multi-sheet surface by the collected data. A two-dimensional image reconstruction is performed on data from all of the sheets together and then a system of linear equations is solved to recover the image at each point in the object. In X-ray tomography systems such as Real Time Tomography (RTT) system comprising multiple sources, the source trajectory is not limited to a helical path relative to an object being imaged. By varying a firing order of the sources and the rate of translation of the object relative to the source and detector array an effect equivalent to a source trajectory approximating a multi-threaded helix of variable pitch can be obtained. It should be noted that any other trajectory can be obtained depending upon the firing order of the sources and thus the invention is not limited to a multi-threaded helix. In one embodiment of the present invention, a complete set of sources is fired before any one source is fired for a second or subsequent time, and the object is translated only in one direction.

In one embodiment of the present invention, z represents a coordinate in an axial direction which is the direction of the translation of the object; x and y represent a coordinate system on a trans-axial plane which is a plane orthogonal to the direction of the translation of the object; and $\lambda$ represents a variable that is used to parameterize a curve which is monotonically increasing in z and passes through each source location in a tomography system such as RTT system in the order of their firing.

The following equation:

$$a(\lambda)=(a_1(\lambda),a_2(\lambda),a_3(\lambda)) \quad (1)$$

represents a curve encircling the region of interest. In one embodiment, in a tomography system such as the RTT, it is a curve having a radius equal to the radius of a ring of sources. In an embodiment where the sources approximate a helical trajectory, $\lambda$ is proportional to the angular polar coordinate in the trans-axial plane.

In various embodiments, irrespective of the actual shape of the detector array, the rays through the source point $a(\lambda)$ are parameterized by Cartesian coordinates on a plane through the z-axis normal to $(a_1(\lambda), a_2(\lambda), 0)$. This plane is termed as a virtual detector plane and Cartesian coordinates (u, v) are used on this plane. For each $\lambda$ and u, a ray given by a rebinning row function $v=V(\lambda, u)$, and a surface that is the graph of a function $\zeta(x, y)$, is chosen. Persons of ordinary skill in the art would know how to obtain an optimal surface C and rebinning function V.

A three dimensional image $f(x,y,z)$ is reconstructed as a series of images on surfaces $\zeta_0(x, y)$, prescribed by the following function for multiple $\lambda_0$:

$$f_{80_0}(x,y)=f(x,y,\zeta_{\lambda_0}(x,y)) \quad (2)$$

where: $x^2+y^2<R_{FOV}^2$; and $R_{FOV}$ represents a radius of the field of view.

Assuming a continuous source trajectory, a known algorithm for rebinning surfaces, and a function generation for helical cone beam computer tomography minimizes the following function:

$$Q(V_0, \zeta_0) = \int_{\lambda_0-\pi/2-\delta}^{\lambda_0+\pi/2+\delta} d\lambda \int_{-u_m}^{u_m} du \int_{l_0(u)-\Delta(u)}^{l_0(u)+\Delta(u)} dl \frac{p(u,\lambda)}{l} (\delta z(\lambda, u, l))^2 \quad (3)$$

where:

$$\delta z(\lambda,u,l) = h\lambda + lV_0(\lambda,u) - \zeta_0(X(\lambda,u,l), Y(\lambda,u,l)); \quad (4)$$

and p is a Parker weight.

Equation 3 may be solved with the following convergent iteration:

$$V_0(\lambda, u) = \frac{1}{2 l_0(u)\Delta l(u)} \int_{l_0(u)-\Delta l(u)}^{l_0(u)+\Delta l(u)} dl (\zeta_0(X(\lambda, u, l), Y(\lambda, u, l)) - h\lambda) \quad (5)$$

$$\zeta_0(x, y) = \quad (6)$$
$$\frac{1}{\int d\lambda p(U, \lambda)/L^2} \int_{\lambda_0-\pi/2-\delta}^{\lambda_0+\pi/2+\delta} d\lambda \frac{p(U(x, y, \lambda), \lambda)}{L(x, y, \lambda)^2} (h\lambda + V_0(U, \lambda)L)$$

Figure 3:
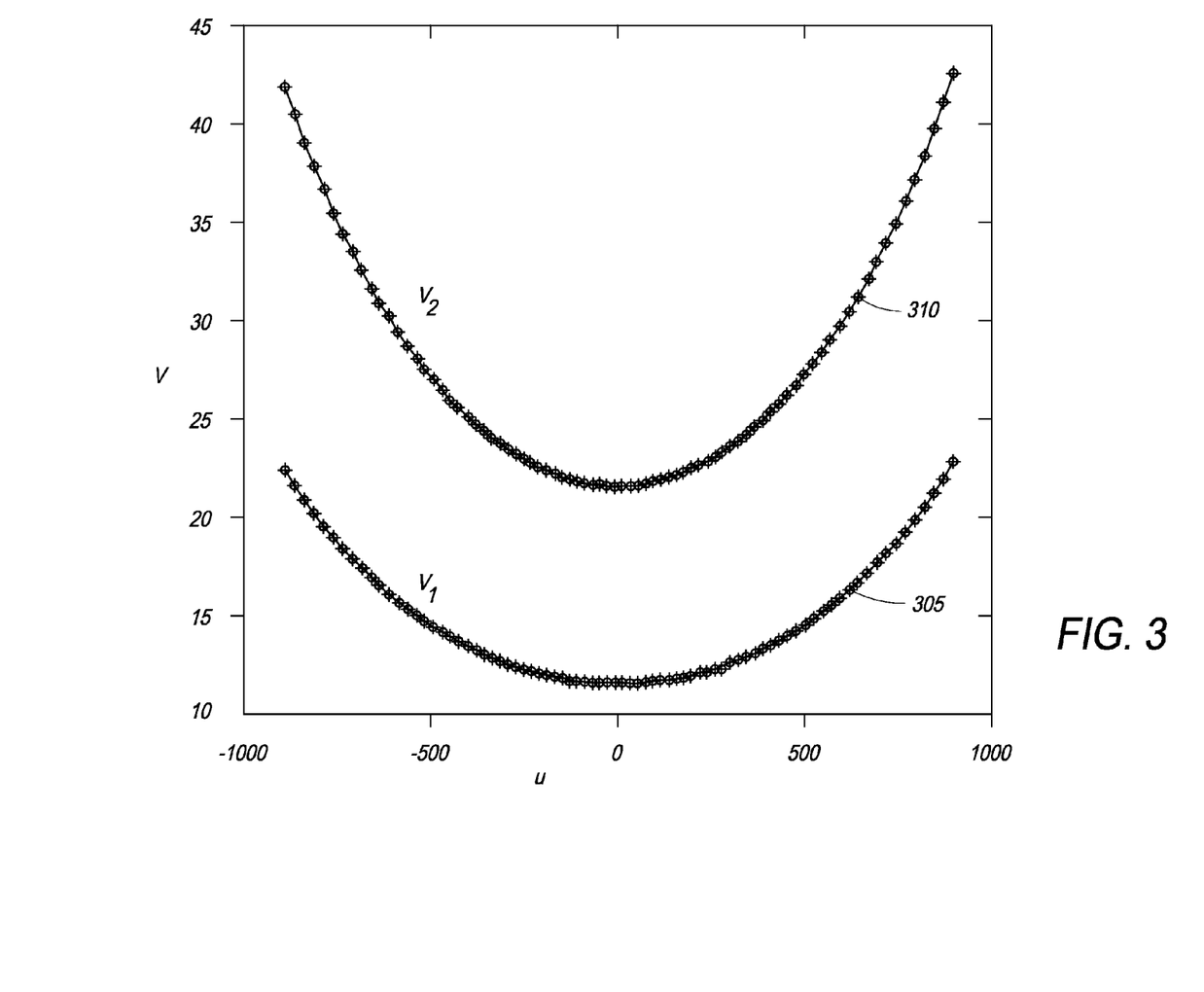
FIG. 3 is a graphical representation of the lower and upper bounds constricting the measurable rays, in an example where data is obtained using the RTT system.

In a tomography system such as the RTT system, the location of the detector array relative to the source poses a constraint on the measurement of rays. When the detector array is projected on to a virtual detector plane the rays that can be measured are constrained by a lower bound $v_1(\lambda, u)$ and an upper bound $v_2(\lambda, u)$. FIG. 3 is a graphical representation of the lower and upper bounds 305 and 310, respectively, constricting the measurable rays.

In an embodiment of the present invention, constraints are accommodated on the detector for a system with a truncated or offset detector array $v_1(\lambda, u) \leq V_0(\lambda, u) \leq v_2(\lambda, u)$ by using Lagrange multipliers $\mu_1$ and $\mu_2$. In order to accommodate an arbitrary firing order the continuous source trajectory is replaced by a set of fired sources $S_A$, where $S_A$ contains sources with $\lambda \in [\lambda_0-\pi/2-\delta, \lambda_0+\pi/2+\delta]$ for each rebinning center $\lambda_0$.

$$Q(\zeta_0, V_0) = \sum_{\lambda \in S_A} \int_{-u_m}^{u_m} du \int_{l_0(u)-\Delta l(u)}^{l_0(u)+\Delta l(u)} dl w(\lambda, u, l) |\delta z(\lambda, u, l)|^q + \quad (7)$$
$$\mu_1(v_1 - V_0) + \mu_2(V_0 - v_2)$$

where:

$$\delta z(\lambda,u,l) = z(\lambda) + lV_0(\lambda,u) - \lambda_0(X(\lambda,u,l), Y(\lambda,u,l)) \quad (8)$$

where $z(\lambda)$ gives the z-translation of the source at the moment it fires. The exponent $q \geq 1$ determines the norm to be minimized or other measure for $0 < q < 1$. In the simplest case $q=2$ where the mean square axial deviation of rays from the rebinning surface the objective function is:

$$Q(V_0, \zeta_0) = \sum_{\lambda \in S_A} \int_{-u_m}^{u_m} du \int_{l_0(u)-\Delta(u)}^{l_0(u)+\Delta(u)} dl \frac{p(u,l)}{l} (\delta z(\lambda, u, l))^2 + \quad (9)$$
$$\mu_1(v_1 - V_0) + \mu_2(V_0 - v_2)$$

Equation (9) may be solved by using convergent iteration as follows:

$$\tilde{V}_0(\lambda, u) = \frac{1}{2 l_0(u)\Delta l(u)} \int_{l_0(u)-\Delta l(u)}^{l_0(u)+\Delta l(u)} dl (\zeta_0(X(\lambda, u, l), Y(\lambda, u, l)) - z(\lambda)) \quad (10)$$

$$V_0(\lambda, u) = \begin{cases} \tilde{V}_0(\lambda, u) & v_1(\lambda, u) \leq \tilde{V}_0(\lambda, u) \leq v_2(\lambda, u) \\ v_1(\lambda, u) & \tilde{V}_0(\lambda, u) < v_1(\lambda, u) \\ v_2(\lambda, u) & \tilde{V}_0(\lambda, u) > v_2(\lambda, u) \end{cases} \quad (11)$$

$$\zeta_0(x, y) = \frac{1}{\sum_{s \in S_A} p(U, \lambda)/L^2} \sum_{\lambda \in S_A} \frac{p(U(x, y, \lambda), \lambda)}{L(x, y, \lambda)^2} (z(\lambda) + V_0(U, \lambda)L) \quad (12)$$

Figure 2:
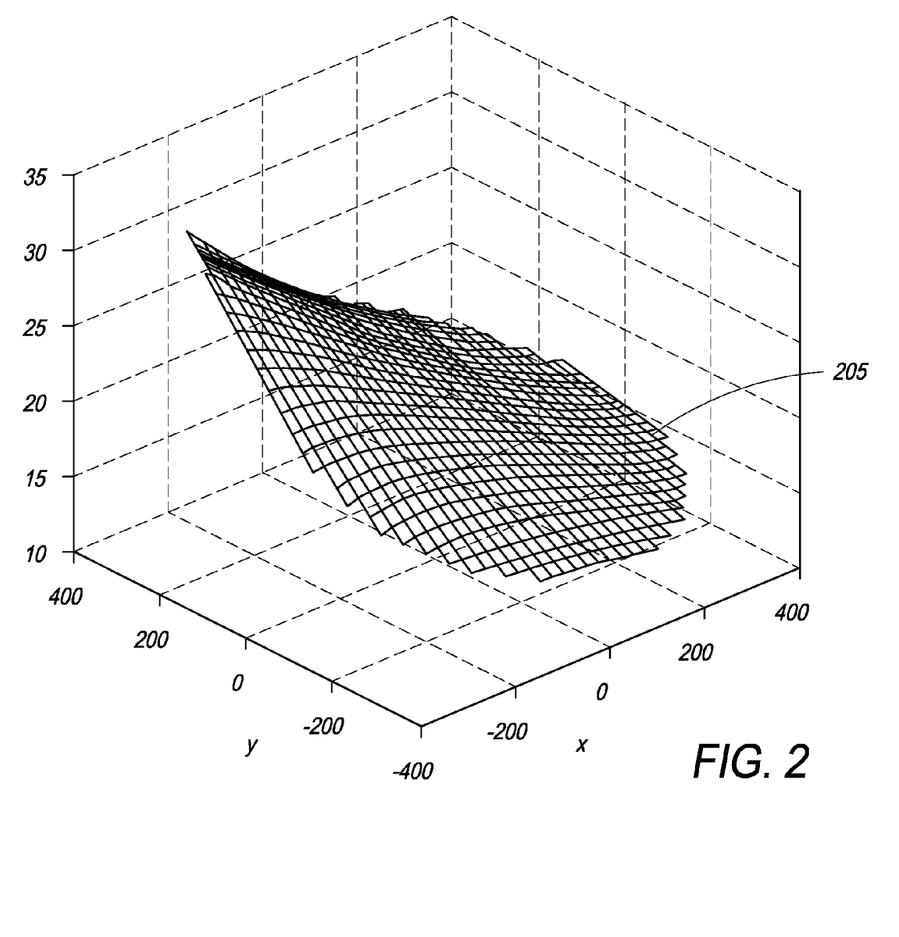
FIG. 2 is a graphical representation of an optimal single rebinning surface for an exemplary RTT geometry.

FIG. 2 is a graphical representation of an optimal single rebinning surface 205 for the RTT geometry.

In various embodiments of the present invention, a set of equations analogous to Equations (1), (2) and (7) through (12) are used for the construction of an optimal multi-sheet surface as well. For the purpose of illustration only, the procedure for a two sheet surface is described. In this case, the same cost functional is minimized and one rebinning function and two rebinning surfaces are obtained, here $S_A$ contains sources with $\lambda \in [\lambda_0-\pi, \lambda_0+\pi]$ for each rebinning center $\lambda_0$.

$$Q(\zeta_0, V_0) = \sum_{\lambda \in S_A} \int_{-u_m}^{u_m} du \int_{l_0(u)-\Delta l(u)}^{l_0(u)} dl w^s(\lambda, u, l) |\delta z^s(\lambda, u, l)|^p + \quad (13)$$
$$\int_{l_0(u)}^{l_0(u)+\Delta l(u)} dl w^s(\lambda, u, l) |\delta z^s(\lambda, u, l)|^p + \mu_1(v_1 - V_0^s) + \mu_2(V_0^s - v_2)$$

where $$\delta z^s(\lambda,u,l) = z(\lambda) + lV_0(\lambda,u) - \zeta_0^s(X(\lambda,u,l), Y(\lambda,u,l)) \quad s \in \{b, t\} \quad (14)$$

and the two sheets of the surface are denoted by $\zeta_b(x, y)$, representing the bottom surface and $\zeta_t(x, y)$, representing the top surface.

Provided below is a derivation of a particular set of weights which fit the approximation that is being made in the method, but the principle holds for any set of positive weights. The case p=2 is used because it yields the strictly convex objective function which has a unique global minimum which can be found by means of a globally convergent iteration. However, other choices of p are plausible e.g. p=1 which would punish outliers less. In principle, once the solution of the least squares problem can be obtained any $p \geq 1$ norm fit can be obtained by, for example, the iteratively reweighted least squares method or p>0 by iteratively reweighted $L_1$ method.

In the particular case of p=2, the square axial deviation reads $$Q(\zeta_0, V_0) = \sum_{\lambda \in S_A} \int_{-u_m}^{u_m} du \int_{l_0(u)-\Delta l(u)}^{l_0(u)} dl \left( \frac{1}{l} + \frac{1}{2l_o - l} \right) (\delta^b z(\lambda, u, l))^2 + \quad (15)$$
$$\int_{l_0(u)}^{l_0(u)+\Delta l(u)} dl \left( \frac{1}{l} + \frac{1}{2l_o - l} \right) (\delta^t z(\lambda, u, l))^2 + \mu_1(v_1 + V_0) + \mu_2(V_0 - v_2)$$

This can again be solved by the following globally convergent alternating iteration.

$$\tilde{V}_0(\lambda, u) = \frac{1}{4l_0(u)^2 \ln\left(\frac{l_0 + \Delta l}{l_0 - \Delta l}\right) - 4l_0(u)\Delta l(u)} \times \quad (16)$$

$$\left(\int_{l_0(u)-\Delta l(u)}^{l_0 u} dl\left(1 + \frac{l}{2l_o - l}\right)(\zeta_0^b(X(\lambda, u, l), Y(\lambda, u, l)) - z(\lambda)) + \right.$$

$$\left.\int_{l_0(u)}^{l_0(u)+\Delta l(u)} dl\left(1 + \frac{l}{2l_o - l}\right)(\zeta_0^t(X(\lambda, u, l), Y(\lambda, u, l)) - z(\lambda))\right)$$

$$V_0(\lambda, u) = \begin{cases} \tilde{V}_0(\lambda, u) & v_1(\lambda, u) \le \tilde{V}_0(\lambda, u) \le v_2(\lambda, u) \\ v_1(\lambda, u) & \tilde{V}_0(\lambda, u) < v_1(\lambda, u) \\ v_2(\lambda, u) & \tilde{V}_0(\lambda, u) > v_2(\lambda, u) \end{cases} \quad (17)$$

$$\zeta_0^s(x, y) = \frac{1}{\sum_{\lambda \in S_A}(1/L^2 + 1/(L(2L_0 - L))} \times \quad (18)$$

$$\sum_{\lambda \in S_a}\left(\frac{1}{L^2} + \frac{1}{L(2L_0 - L)}\right)(z(\lambda) + LV_0(\lambda, U)),$$

where $L \le L_0$ for $s=b$ and $L \ge L_0$ for $s=t$.

Figure 1:
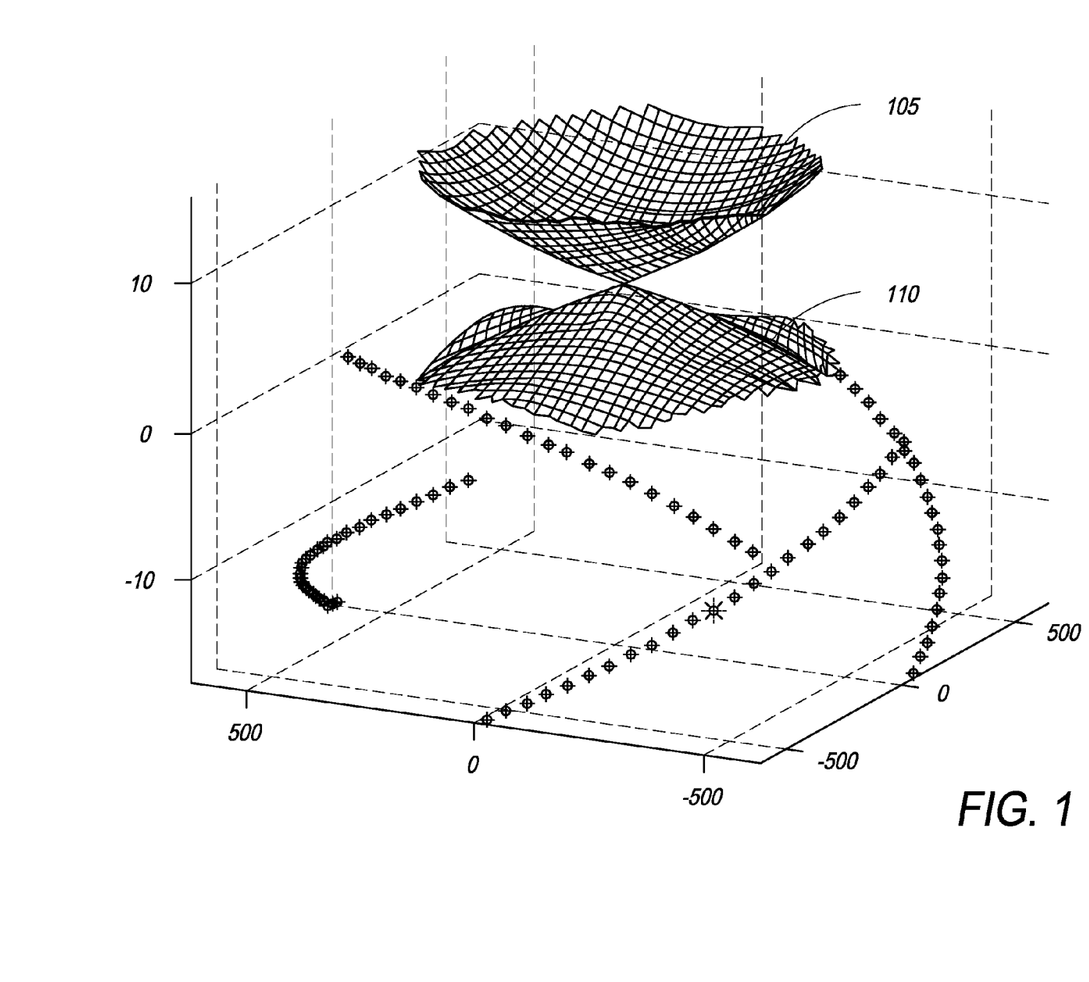
FIG. 1 is a graphical representation of a typical optimal rebinning surface with two sheets.

FIG. 1 is a graphical representation of a typical optimal rebinning surface with two sheets, 105 and 110.

With the two sheet surface $\zeta_0^s$, $s \in \{t, b\}$ on each sheet of the surface $\zeta_0^s$ we define the following 2D fan beam transform:

$$p_0^s(\lambda,u) = \sqrt{R^2+u^2}\int_{l_0(u)-\Delta l(u)}^{l_0(u)+\Delta l(u)} dl \zeta_0^s(X(\lambda,u,l),Y(\lambda,u,l)). \quad (19)$$

Then, the 2D fan beam transform on the entire surface $\zeta_0$ (including all its sheets) is the superposition of the fan beam transforms on all the individual sheets $$p_0(\lambda, u) = \sum_s p_0^s(\lambda, u), s \in \{t, b\} \quad (20)$$

We also define the following mixed 2D fan beam transform on the multi-sheet surface $\zeta_0$ $$\tilde{g}_0(\lambda,u) = \tilde{g}_0^b(\lambda,u) + \tilde{g}_0^t(\lambda,u),$$

where $$\tilde{g}_0^b(\lambda,u) = \sqrt{R^2+u^2}\int_{l_0(u)-\Delta l(u)}^{l_0(u)} dl \zeta_0^b(X(\lambda,u,l),Y(\lambda,u,l))$$

$$\tilde{g}_0^t(\lambda,u) = \sqrt{R^2+u^2}\int_{l_0(u)}^{l_0(u)+\Delta l(u)} dl \zeta_0^t(X(\lambda,u,l),Y(\lambda,u,l)) \quad (20)$$

Note, that the first integral is taken over $\zeta_0^b$ and the second over $\zeta_0^t$. This mixed fan beam transform is a quantity which is the closest to the cone beam data as measured by the RTT. The idea of multi-sheet surface rebinning methods is to approximate $\tilde{g}_0$ by the rebinned data $g_0$.

$$\tilde{g}_0(\lambda,u) \approx g_0(\lambda,u), \quad (22)$$

Where $g_0$ denotes the cone beam data which were rebinned to the surface $\zeta_0$ using the rebinning function $V_0$.

$$g_0(\lambda,u) = (\lambda,u) = \sqrt{R^2+u^2}\int_{l_0(u)-\Delta l(u)}^{l_0(u)+\Delta l(u)} dl f(X(\lambda,u,l),Y(\lambda,u,l),z(\lambda)+lV_0(\lambda,u)) \quad (23)$$

With analogous splitting $$g_0(\lambda,u) = g_0^b(\lambda,u) + g_0^t(\lambda,u),$$

where $$g_0^b(\lambda,u) = \sqrt{R^2+u^2}\int_{l_0(u)-\Delta l(u)}^{l_0(u)} dl f(X(\lambda,u,l),Y(\lambda,u,l),z(\lambda)+lV_0(\lambda,u))$$

$$g_0^t(\lambda,u) = \sqrt{R^2+u^2}\int_{l_0(u)}^{l_0(u)+\Delta l(u)} dl f(X(\lambda,u,l),Y(\lambda,u,l),z(\lambda)+lV_0(\lambda,u)) \quad (24)$$

it holds $$p_0^s(\lambda,u) = \tilde{g}_0^s(\lambda,u) + \tilde{g}_0^s(\lambda_c,u_c) \approx g_0^s(\lambda,u) + g_0^s(\lambda_c,u_c),$$
$$s \in \{b,t\} \quad (25)$$

where $(\lambda_c, u_c)$ denotes the ray along the same line as $(\lambda, u)$ but traveling in the opposite direction. It therefore follows:

$$p_0(\lambda,u) = p_0^b(\lambda,u) + p_0^t(\lambda,u) = \tilde{g}_0(\lambda,u) + \tilde{g}_0(\lambda_c,u_c) \approx g_0(\lambda,u) + g_0(\lambda_c,u_c) \quad (26)$$

This equation shows that both $p_0(\lambda, u)$ and $\tilde{g}_0(\lambda, u) + \tilde{g}_0(\lambda_c, u_c)$ describe the same 2D fan beam transform on the multi-sheet surface $\zeta_0$ (i.e., on all its sheets). Since we have a way to approximate the latter, we can approximate $p_0(\lambda, u)$ as well. Due to the linearity of the ray transform, $p_0$ is also the 2D fan beam transform of superposition of the objects on all sheets of the surface $\zeta_0$. This fact is then used to recover the volumetric density function $f$ via deconvolution.

In an exemplary scenario, the constraint on the detector is such that only upward directed rays are detected. Hence, $a_3(\lambda) < v_1(\lambda, 0)$. The intersection of the ray with the region of interest is divided into two equal intervals; an interval closer to $a(\lambda)$ where the ray is close to the surface $\zeta_b$, and another interval where it is closer to $\zeta_t$.

Figure 4:
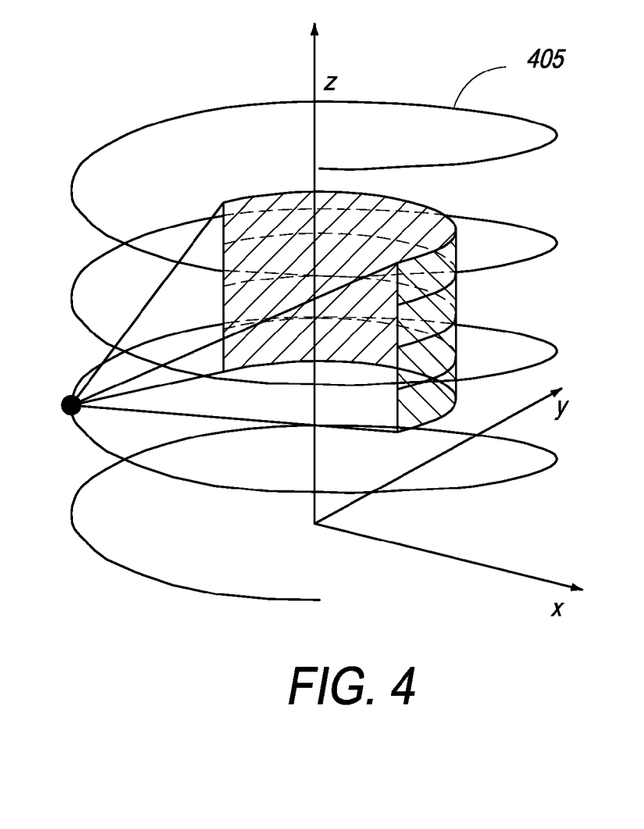
FIG. 4 depicts a standard truncated cone beam source.
Figure 5:
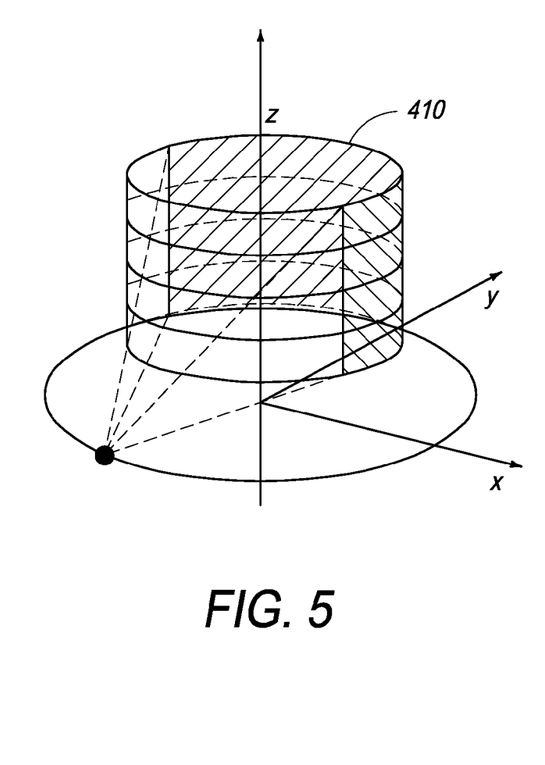
FIG. 5 depicts an offset geometry system such as the RTT.

FIG. 4 is a graphical representation of a standard truncated cone beam source 405 and FIG. 5 is a graphical representation of an offset geometry system 410, such as the RTT. In an embodiment of the present invention, the optimal choice of double-sheet surface that minimizes the total Q over both sheets is found to be in the shape roughly like a two pointed cone as illustrated in FIG. 1. Each voxel lies on the intersection of some sheets for different multi-sheet surfaces. Each point value on the multi-sheet surface is a sum of point values on all sheets or a sum of the entire z-direction neighborhoods of the points on the sheets weighted with Point Spread Functions (PSF) of the sheets. This results in a sparse system of simultaneous equations to be solved for recovering the value of $f(x,y,z)$ at a specific voxel. In the simplest discretization, each row of this system of equations would have only two non-zero entries. Modelling PSF of the sheets and incorporating it into the matrix results in a slightly less sparse but more stable system. For conventional rebinning, known ultra-hyperbolic equations can be used to improve the accuracy of approximation and this can also be applied to multi-sheet surface rebinning.

Hence, the present invention provides a tomography system and method in which the reconstruction of a three dimensional image is performed by collecting data from rays close to a surface with more than one sheet. A two-dimensional properly weighted inverse Radon transform is applied to the combined data from all sheets of one multi-sheet surface. This is repeated for a number of multi-sheet surfaces with rebinning centers chosen among fired sources. In one embodiment, the rebinning centers are equispaced in the z-direction, and their number is at least as large as the required z-resolution resulting in more than one sheet passing through each point in the region to be imaged. A system of simultaneous equations with a matrix, which one row involves information about where each sheet of one surface intersects the region to be imaged is then solved to produce a three dimensional image. The properties of this system, including independence of points in xy-plane, only local dependence on the z variable or possibility of precomputing many quantities mean that it can be solved efficiently.

The system is possibly ill-conditioned or right hand sides contain errors hence regularization is needed and a regularization parameter needs to be selected. Regularization methods that can be employed include quadratic penalty methods such as Tikhonov regularization, generalized Tikhonov regularization using a quadratic penalty applied to a weighted sum of derivatives, using any weighted norm of any order of derivatives including 0, the iterative regularization, total variation regularization, nonnegativity constraints, or using any type of sparsity constraints in different bases, including Curvelets or Wavelets. Possible methods for solution of the regularized system include a least squares sense, a minimization of a sum of absolute values of residuals, a minimization of any weighted norm of residuals, a minimization of any weighted norm of residuals where said weights are derived from a model of data errors, (structured) Total Least Norms, Iteratively Reweighted Least Squares and Iteratively Reweighted Norm approaches, and optimization methods, including primal-dual methods, gradient methods, gradient projection methods, nonlinear reconstruction methods. The regularization parameter can be chosen differently for different blocks of equations using methods including L-curve, Generalized Cross Validation and Unbiased Predictive Risk Estimation. Different grid sizes can be employed for different quantities at all stages resulting in efficiency increase or additional stability, examples include coarse grid matrix modeling leading to problems with multiple right hand sides or simultaneous regularization in the z-direction and within blocks in the xy-plane. Approximations leading to further symmetries may lead to even more memory and computationally efficient solutions.

It should be appreciated that the analytical methods described herein are performed by a controller, which has at least one processor executing a plurality of programmatic instructions embodying the analytical methods described herein. The instructions, along with the requisite data, are stored in a memory that is accessible to the processor in either a remote or local configuration. The input data is obtained from one or more detectors integrated into an X-ray scanning system.

While the exemplary embodiments of the present invention are described and illustrated herein, it will be appreciated that they are merely illustrative. It will be understood by those skilled in the art that various changes in form and detail may be made therein without departing from or offending the spirit and scope of the invention.

We claim:

1. A controller adapted to process X-rays detected by a plurality of detectors and generate a three dimensional image wherein said controller comprises a plurality of programmatic instructions that, when executed, rebin detected X-rays onto a non-flat surface by using data from said plurality of detectors to approximate a combination of measured data from a first line and a second line, wherein the first and second lines intersect, wherein the first line defines a first surface, and wherein the second line defines a second surface, and using the combination to solve at least two simultaneous equations to determine values of each point in the three dimensional image such that each point lies in at least one of the first surface and the second surface.

2. The controller of claim 1 wherein said controller filters said rebinned data to maximize resolution of said three dimensional image.

3. The controller of claim 1 wherein said rebinning of the detected X-rays onto a non-flat surface is achieved by collecting data from X-rays close to a surface with more than one sheet.

4. The controller of claim 3 wherein reconstruction on each said surface is subsequently achieved by applying at least one of a two-dimensional weighted inverse Radon transform or an adapted two-dimensional reconstruction, to combined data from all sheets.

5. The controller of claim 1 wherein the more than two simultaneously solvable equations relate to a plurality of reconstructed superimposed images, one on each of a plurality of multi-sheet surfaces, and a plurality of z-positions of sheets of each multi-sheet surface intersecting each point in a region being imaged.

6. The controller of claim 5 wherein the more than two simultaneously solvable equations relate to a plurality of z-positions of sheets of each multi-sheet surface intersecting each point in a region being imaged.

7. The controller of claim 1 wherein said simultaneously solvable equations is solved using at least one of a least squares sense, a minimization of a sum of absolute values of residuals, a minimization of any weighted norm of residuals, a minimization of any weighted norm of residuals wherein said weights are derived from a model of data errors, structured Total Least Norms, Iteratively Reweighted Least Squares and Iteratively Reweighted Norm approaches, or optimization methods including primal-dual methods, gradient methods, gradient projection methods, nonlinear reconstruction methods, with any type of regularization, penalty or constraints.

8. The controller of claim 1 wherein the controller initiates the generation of said three dimensional image after a threshold amount of detected X-ray data are obtained prior to obtaining data for the entire object.

9. The controller of claim 1 wherein the plurality of X-ray sources are stationary.

10. The controller of claim 1 wherein said controller uses said simultaneous equations to improve approximation with detected X-rays which were at least partially not on a rebinning surface.

11. The controller of claim 1 wherein said controller is adapted to perform backprojection without filtering on multi-sheet surfaces.

12. The controller of claim 11 wherein said controller is adapted to perform axial deconvolution.

13. The controller of claim 12 wherein said controller is adapted to filter each transaxial slice of a volume being imaged.

14. The controller of claim 1, wherein said controller is adapted to correct sinogram data on a rebinning surface.

15. A method of generating a three dimensional image in a tomography system having a plurality of X-ray sources and a plurality of detectors comprising: rebinning each of said detected X-rays onto a non-flat surface by using data from said plurality of detectors to approximate data from at least two intersecting lines, wherein each of said intersecting lines is associated with a surface, and using the approximated data to solve two or more simultaneous equations to determine values of each point in the three dimensional image such that each point lies in at least one of the surfaces associated with each of the at least two intersecting lines.

16. The method of claim 15 further comprising filtering said rebinned data to maximize resolution of said three dimensional image.

17. The method of claim 15 wherein the simultaneously solvable equations relate to a plurality of reconstructed superimposed images, one on each of a plurality of multi-sheet surfaces.

18. The method of claim 15 wherein the simultaneously solvable equations relate to a plurality of z-positions of sheets of each multi-sheet surface intersecting each point in a region being imaged.

19. The method of claim 15 wherein said approximation is a combination of measured data from a first line and a second line.

* * * * *